(12) United States Patent
Lins

(10) Patent No.: US 10,779,958 B2
(45) Date of Patent: Sep. 22, 2020

(54) SACROILIAC JOINT FUSION SYSTEMS AND METHODS

(71) Applicant: Beacon Biomedical, LLC, Jupiter, FL (US)

(72) Inventor: Robert E. Lins, Boca Raton, FL (US)

(73) Assignee: Beacon Biomedical, LLC, Jupiter, FL (US)

( * ) Notice: Subject to any disclaimer, the term of this patent is extended or adjusted under 35 U.S.C. 154(b) by 151 days.

(21) Appl. No.: 14/882,792

(22) Filed: Oct. 14, 2015

(65) Prior Publication Data

US 2016/0175113 A1 Jun. 23, 2016

Related U.S. Application Data

(60) Provisional application No. 62/095,120, filed on Dec. 22, 2014, provisional application No. 62/118,759, filed on Feb. 20, 2015.

(51) Int. Cl.
| | |
|---|---|
| *A61B 17/70* | (2006.01) |
| *A61B 17/02* | (2006.01) |
| *A61B 17/88* | (2006.01) |
| *A61F 2/46* | (2006.01) |
| *A61B 17/17* | (2006.01) |
| *A61F 2/30* | (2006.01) |

(52) U.S. Cl.
CPC ........ *A61F 2/4601* (2013.01); *A61B 17/1757* (2013.01); *A61F 2002/30995* (2013.01)

(58) Field of Classification Search
CPC ............ A61B 17/7055; A61B 17/1757; A61B 17/1671; A61B 17/864; A61B 17/8685; A61B 17/1615; A61B 17/84; A61B 2017/564; A61B 17/637
See application file for complete search history.

(56) References Cited

U.S. PATENT DOCUMENTS

| | | |
|---|---|---|
| 697,209 A | 4/1902 | Koppenhagen |
| 5,334,205 A | 8/1994 | Cain |
| 5,679,550 A | 10/1997 | Yoshimura et al. |
| 5,690,711 A | 11/1997 | Bosses |
| 5,874,957 A | 2/1999 | Cline et al. |

(Continued)

FOREIGN PATENT DOCUMENTS

WO 2012-036872 A2 3/2012

*Primary Examiner* — Ann Schillinger
(74) *Attorney, Agent, or Firm* — McHale & Slavin, P.A.

(57) ABSTRACT

Joint fixation systems and methods, enabling: drilling one or more major bores in a joint; drilling one or more minor bores in the joint, wherein the one or more minor bores are disposed about a periphery of and partially overlap the major bore(s); and disposing an implant in the major bore(s) and the one or more minor bores, wherein a cross-sectional shape of the implant substantially conforms to a collective cross-sectional shape of the major bore(s) and the one or more minor bores. Prior to drilling the major bore(s) or the one or more minor bores, a portal tube is disposed adjacent to the joint, thereby providing access to and stabilizing the joint. A drill guide tube is disposed concentrically within the portal tube, and a drill guide is disposed concentrically within the drill guide tube. Subsequent to drilling the major bore(s) and the one or more minor bores, an implant guide tube is disposed concentrically within the portal tube.

12 Claims, 12 Drawing Sheets

(56) References Cited

U.S. PATENT DOCUMENTS

| | | |
|---|---|---|
| 5,899,908 A | 5/1999 | Kuslich et al. |
| 5,950,604 A | 9/1999 | Inamijima |
| 6,009,651 A | 1/2000 | Current |
| 6,016,364 A | 1/2000 | Kikuchi et al. |
| 6,440,139 B2 | 8/2002 | Michelson |
| 6,534,878 B1 | 3/2003 | Sander et al. |
| 7,083,623 B2 | 8/2006 | Michelson |
| 7,635,370 B2 | 12/2009 | Michelson |
| 7,648,509 B2 | 1/2010 | Stark |
| 8,066,709 B2 | 11/2011 | Michelson |
| 8,109,934 B2 | 2/2012 | Guenther et al. |
| 8,221,428 B2 | 7/2012 | Trieu |
| 8,348,950 B2 | 1/2013 | Assell et al. |
| 8,454,618 B2 | 6/2013 | Stark |
| 8,663,232 B2 | 3/2014 | Michelson |
| 8,734,456 B2 | 5/2014 | Stark |
| 8,740,912 B2 | 6/2014 | Stark |
| 8,808,377 B2 | 8/2014 | Donner |
| 8,882,818 B1 | 11/2014 | Vestgaarden |
| 8,979,928 B2 | 3/2015 | Donner |
| 9,017,407 B2 | 4/2015 | Donner |
| 9,314,232 B2 | 4/2016 | Stark |
| 9,333,090 B2 | 5/2016 | Donner et al. |
| 9,345,589 B2 | 5/2016 | Stark |
| 2007/0270879 A1 | 11/2007 | Isaza et al. |
| 2008/0009861 A1 | 1/2008 | Stark |
| 2009/0099610 A1 | 4/2009 | Johnson et al. |
| 2009/0259261 A1 | 10/2009 | Reiley |
| 2010/0010496 A1 | 1/2010 | Isaza et al. |
| 2010/0106200 A1 | 4/2010 | Stark |
| 2010/0131011 A1 | 5/2010 | Stark |
| 2011/0166575 A1 | 7/2011 | Assell et al. |
| 2011/0238181 A1* | 9/2011 | Trieu ................ A61B 17/1735 623/17.11 |
| 2011/0264225 A1 | 10/2011 | Michelson |
| 2011/0264229 A1 | 10/2011 | Donner |
| 2012/0022535 A1* | 1/2012 | Mayer ................ A61B 17/1682 606/75 |
| 2012/0316565 A1 | 12/2012 | Stark |
| 2013/0026206 A1 | 1/2013 | Fox |
| 2013/0030456 A1 | 1/2013 | Assell et al. |
| 2013/0035723 A1 | 2/2013 | Donner |
| 2013/0144343 A1 | 6/2013 | Srnett et al. |
| 2013/0197590 A1 | 8/2013 | Assell et al. |
| 2013/0226181 A1 | 8/2013 | Assell et al. |
| 2013/0245703 A1 | 9/2013 | Warren et al. |
| 2013/0282012 A1 | 10/2013 | Stark |
| 2014/0031935 A1 | 1/2014 | Donner et al. |
| 2014/0088596 A1 | 3/2014 | Assell et al. |
| 2014/0142700 A1 | 5/2014 | Donner et al. |
| 2014/0200618 A1* | 7/2014 | Donner ............. A61B 17/1757 606/281 |
| 2014/0236310 A1 | 8/2014 | Stark |
| 2014/0257415 A1 | 9/2014 | Reiley |
| 2014/0277165 A1 | 9/2014 | Katzman et al. |
| 2014/0277460 A1 | 9/2014 | Schifano et al. |
| 2014/0277463 A1 | 9/2014 | Yerby et al. |
| 2014/0336763 A1 | 11/2014 | Donner et al. |
| 2015/0088200 A1* | 3/2015 | Lins .................. A61B 17/7064 606/247 |
| 2015/0112444 A1 | 4/2015 | Aksu |
| 2015/0209087 A1 | 7/2015 | Donner |
| 2015/0250611 A1 | 9/2015 | Schifano et al. |
| 2015/0250612 A1 | 9/2015 | Schifano et al. |

* cited by examiner

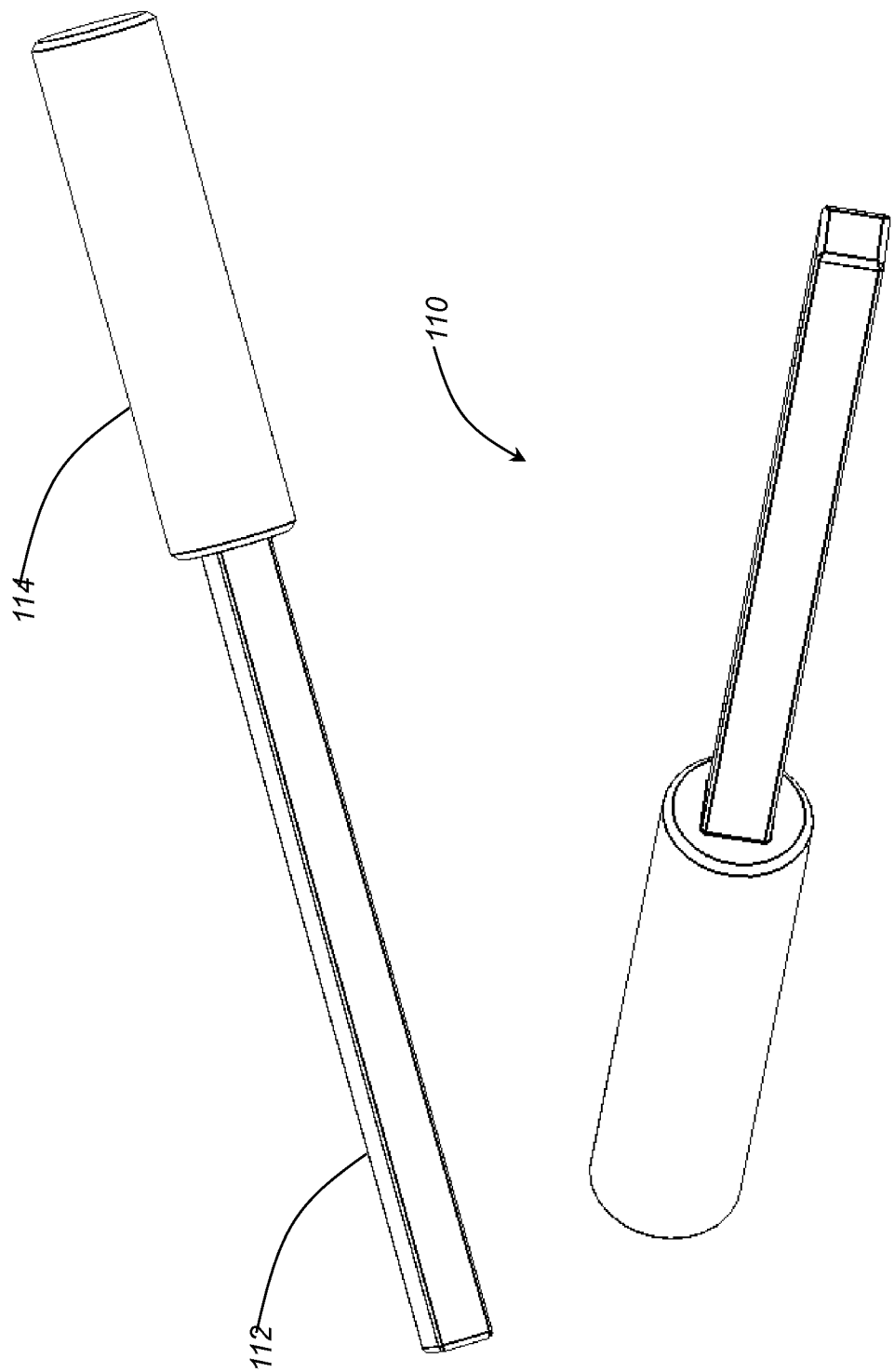

SACROILIAC JOINT FUSION SYSTEMS AND METHODS

CROSS-REFERENCE TO RELATED APPLICATIONS

The present patent application/patent claims the benefit of priority of U.S. Provisional Patent Application No. 62/095,120, filed on Dec. 22, 2014, and entitled "SACROILIAC JOINT FUSION SYSTEMS AND METHODS," and U.S. Provisional Patent Application No. 61/118,759, filed on Feb. 20, 2015, and entitled "SACROILIAC JOINT FUSION SYSTEMS AND METHODS," the contents of both of which are incorporated in full by reference herein.

FIELD OF THE INVENTION

The present invention relates generally to sacroiliac and other joint fusion systems and methods. More specifically, the present invention relates to a portal tube, a drill guide tube, a drill guide, an implant guide tube, an implant, and related instrumentation for fusing or otherwise securing a sacroiliac or other joint via a minimally-invasive or open surgical procedure.

BACKGROUND OF THE INVENTION

The sacroiliac joint is the joint between the sacrum and the ilium of the pelvis. The sacrum and the ilium are joined by ligaments. The sacrum supports the spine and is supported, in turn, by the ilium on each side. The sacroiliac joint is a synovial joint, with articular cartilage and irregular elevations and depressions that produce interlocking of the sacrum and the ilium.

Pain associated with the sacroiliac joint can be caused by traumatic fracture, dislocation of the pelvis, degenerative arthritis, sacroiliitis, a degenerative condition or inflamation of the sacroiliac joint, osteitis condensans ilii, or the like. Sacroiliac joint fusion is often indicated as a surgical treatment for such conditions. Sacroiliac joint fusion can be performed via an anterior approach, a posterior approach, or a lateral approach, and typically involves the placement of a fixation assembly, an implant, and/or one or more screws. Significant problems exist, especially when sacroiliac joint fusion is performed via an open surgical procedure, for example.

Open surgical procedures require general anesthesia and can involve considerable operative time, recovery time, hospitalization, and pain due to significant soft tissue damage. Damage to blood vessels and nerves is also possible. Specifically, the placement of a fixation assembly, an implant, and/or one or more screws can cause damage to the lumbosacral neurovascular elements and/or delayed union of the sacroiliac joint. In a worst case scenario, this can require revision or removal surgery.

Minimally-invasive surgical procedures are technically more difficult and require multiplanar fluoroscopy/radiography of the articular surfaces of the sacroiliac joint, for example. Again, the placement of a fixation assembly, an implant, and/or one or more screws can cause damage to the lumbosacral neurovascular elements and/or delayed union of the sacroiliac joint. Further, sacral anomalies can lead to mal-placement of the implant, leading to damage to the surrounding structures.

In both open and minimally-invasive surgical procedures, insufficient amounts of the articular surfaces and/or the cortical surfaces of the sacroiliac joint may be removed to relieve pain in the sacroiliac joint. Likewise, insufficient amounts of the articular surfaces and/or the cortical surfaces of the sacroiliac joint may be engaged by the fixation assembly, the implant, and/or the one or more screws to ensure adequate stabilization and/or fusion. The failure to adequately stabilize and/or fuse the sacroiliac joint can result in a failure to relieve the condition being treated. Malalignment of the sacroiliac joint is a similar problem and can lead to increased pain.

Thus, what are still needed in the art are improved sacroiliac joint fusion systems and methods that provide adequate visualization of and access to the sacroiliac joint, provide very predictable and consistent results easily and efficiently, provide adequate stabilization and/or fusion of the sacroiliac joint, as well as optional distraction and/or translation, if desired, and minimize surgical time, thereby eliminating the problems described above.

BRIEF SUMMARY OF THE INVENTION

In various exemplary embodiments, the present invention provides a portal tube, a drill guide tube, a drill guide, and implant guide tube, an implant, and related instrumentation for fusing or otherwise securing a sacroiliac or other joint via a minimally-invasive or open surgical procedure, with direct and/or indirect (i.e. fluoroscopy/radiography) visualization. These sacroiliac joint fusion systems and methods provide superior visualization of and access to the sacroiliac joint, provide very predictable and consistent results easily and efficiently, provide superior stabilization and/or fusion of the sacroiliac joint, as well as optional distraction and/or translation, if desired, and minimize surgical time, thereby eliminating the problems described above.

In one exemplary embodiment, the present invention provides a joint fixation system, including: a portal tube disposed adjacent to a joint (and optionally partially into the joint), thereby providing access to and stabilization of the joint; a drill guide tube selectively disposed concentrically within the portal tube through which: one or more major bores are drilled in the joint; and one or more minor bores are drilled in the joint, wherein the one or more minor bores are disposed about a periphery of and partially overlap the major bore(s); and an implant guide tube selectively disposed concentrically within the portal tube through which an implant is selectively disposed in the major bore(s) and the one or more minor bores, wherein a cross-sectional shape of the implant substantially conforms to a collective cross-sectional shape of the major bore(s) and the one or more minor bores. The portal tube is secured to one of the bony structures forming the joint using a guide pin. The system also includes a drill guide selectively disposed concentrically within the drill guide tube. The implant guide tube defines an internal channel that has a cross-sectional shape that substantially conforms to the cross-sectional shape of the implant, wherein the implant is disposed in the major bore(s) and the one or more minor bores through the internal channel of the implant guide tube. The implant is disposed in the major bore(s) and the one or more minor bores through the implant guide tube using an elongate impaction tool that has a cross-sectional shape that substantially conforms to the cross-sectional shape of the internal channel of the implant guide tube. Optionally, the implant includes one or more recesses configured to hold a bone graft material. Optionally, the joint is a sacroiliac joint. It should be noted that the major bore(s) and the minor bore(s) can have the same relative size, or can be different sizes, although the major bore(s) are typically drilled first. The major bore(s)

and the minor bore(s) can also overlap, or they can simply be drilled adjacent to one another, provided that they remove a bulk of the bony material in a predetermined area that roughly corresponds to the shape of the implant that is eventually inserted into this area by press fitting.

In another exemplary embodiment, the present invention provides a joint fixation method, including: drilling one or more major bores in a joint; drilling one or more minor bores in the joint, wherein the one or more minor bores are disposed about a periphery of and partially overlap the major bore(s); and disposing an implant in the major bore(s) and the one or more minor bores, wherein a cross-sectional shape of the implant substantially conforms to a collective cross-sectional shape of the major bore(s) and the one or more minor bores. The method also includes, prior to drilling the major bore(s) or the one or more minor bores, disposing a portal tube adjacent to the joint (and optionally partially into the joint), thereby providing access to and stabilizing the joint. The method further includes securing the portal tube to one of the bony structures forming the joint using a guide pin. The method still further includes, prior to drilling the major bore(s) or the one or more minor bores, disposing a drill guide tube concentrically within the portal tube. The method still further includes drilling the major bore(s) through the drill guide tube and drilling the one or more minor bores through the drill guide tube. The method still further includes, prior to drilling the one or more minor bores, disposing a drill guide concentrically within the drill guide tube. The method still further includes, subsequent to drilling the major bore(s) and the one or more minor bores, disposing an implant guide tube concentrically within the portal tube. The implant guide tube defines an internal channel that has a cross-sectional shape that substantially conforms to the cross-sectional shape of the implant, wherein the implant is disposed in the major bore(s) and the one or more minor bores through the internal channel of the implant guide tube. The implant is disposed in the major bore(s) and the one or more minor bores through the implant guide tube using an elongate impaction tool that has a cross-sectional shape that substantially conforms to the cross-sectional shape of the internal channel of the implant guide tube. Optionally, the implant includes one or more recesses configured to hold a bone graft material. Optionally, the joint is a sacroiliac joint. Again, it should be noted that the major bore(s) and the minor bore(s) can have the same relative size, or can be different sizes, although the major bore(s) are typically drilled first. The major bore(s) and the minor bore(s) can also overlap, or they can simply be drilled adjacent to one another, provided that they remove a bulk of the bony material in a predetermined area that roughly corresponds to the shape of the implant that is eventually inserted into this area by press fitting.

In a further exemplary embodiment, the present invention provides a joint fixation method, including: drilling a plurality of bores in a joint, wherein the plurality of bores collectively approximate a predetermined cross-sectional shape; and press fitting an implant having the predetermined cross-sectional shape in the plurality of bores drilled in the joint. The method also includes, prior to drilling the plurality of bores, disposing a portal tube adjacent to the joint, thereby providing access to and stabilizing the joint. The method further includes securing the portal tube to the joint using a guide pin. The method still further includes, prior to drilling the plurality of bores, disposing a drill guide tube concentrically within the portal tube and drilling the plurality of bores through the drill guide tube. Optionally, the method still further includes, prior to drilling at least some of the plurality of bores, disposing a drill guide concentrically within the drill guide tube. Optionally, the method still further includes, subsequent to drilling the plurality of bores, disposing an implant guide tube concentrically within the portal tube. The implant guide tube defines an internal channel that has a cross-sectional shape that substantially conforms to the predetermined cross-sectional shape of the implant, wherein the implant is disposed in the plurality of bores through the internal channel of the implant guide tube. Optionally, the implant is disposed in the plurality of bores through the implant guide tube using an elongate impaction tool that has a cross-sectional shape that substantially conforms to the cross-sectional shape of the internal channel of the implant guide tube. Optionally, the implant includes one or more recesses configured to hold a bone graft material. Optionally, the joint is a sacroiliac joint.

BRIEF DESCRIPTION OF THE DRAWINGS

The present invention is illustrated and described herein with reference to the various drawings, in which like reference numbers are used to denote like system components/method steps, as appropriate, and in which:

FIG. 12 is a series of perspective views of one exemplary embodiment of the implant insertion tool of the present invention.

DETAILED DESCRIPTION OF THE INVENTION

Again, in various exemplary embodiments, the present invention provides a portal tube, a drill guide tube, a drill guide, and implant guide tube, an implant, and related instrumentation for fusing or otherwise securing a sacroiliac or other joint via a minimally-invasive or open surgical procedure. These sacroiliac joint fusion systems and methods provide superior visualization of and access to the sacroiliac joint, provide very predictable and consistent results easily and efficiently, provide superior stabilization and/or fusion of the sacroiliac joint, as well as distraction and/or translation, if desired, and minimize surgical time, thereby eliminating the problems described above.

Figure 1:
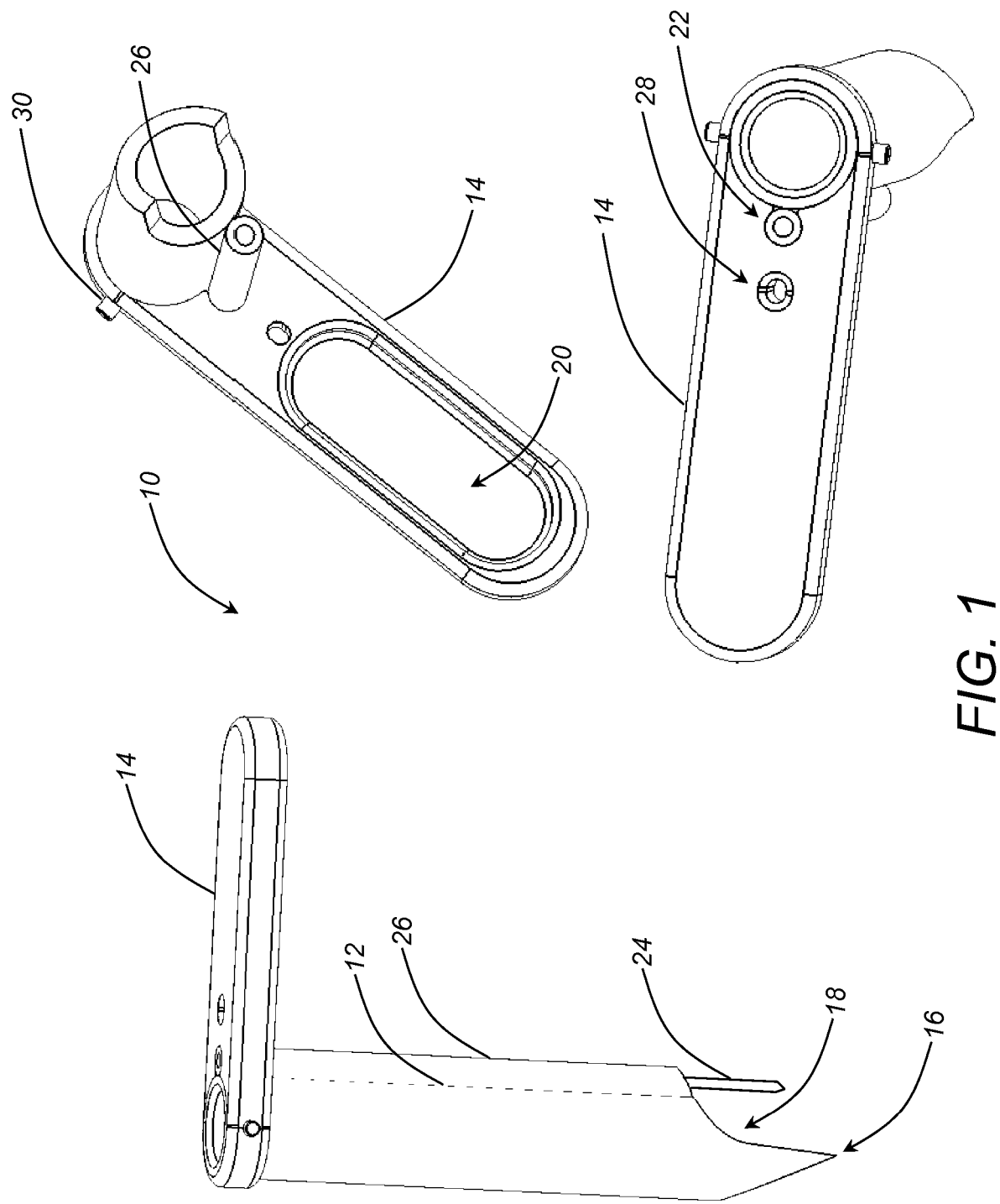
FIG. 1 is a series of perspective views of one exemplary embodiment of the portal tube of the present invention.

Referring now specifically to FIG. 1, in one exemplary embodiment, the portal tube 10 includes a cannulated access tube 12 and a handle 14 coupled to the proximal end of the access tube 12. The handle 14 is used to manipulate the access tube 12, as well as to secure other components inside the access tube 12. All components can be keyed accordingly. The distal end of the access tube 12 includes an angled end 16, optionally including a cut away 18, that is configured and shaped to engage the sacroiliac joint, or another joint, such that the access tube 12 is held in proper alignment, without penetrating too deeply. Preferably, the access tube 12 is made of a surgically compatible metal or plastic, and has a length of between about 120 and about 150 mm, an external diameter of between about 20 and about 25 mm, and an internal diameter of between about 15 and about 20 mm. The handle 14 is a generally paddle shaped component and may include a recess 20, finger contours, etc. The handle 14 includes a first port 22 through which a guide pin 24 is inserted. The access tube 12 includes a corresponding cannulated channel 26 through which the guide pin 24 passes. Preferably, the guide pin 24 includes a shoulder stop (not illustrated) at its proximal end, such that penetration of the guide pin 24 through the channel 26 is limited, and protrudes a predetermined distance beyond the distal end of the channel 26. This protruding portion of the guide pin 24 includes a drill bit or is threaded such that it can penetrate into the bony structure on one side of the joint, thereby securing the access tube 12 to the joint in the proper alignment. The handle 14 also includes a second port 28 that is configured to receive a corresponding pin associated with other components secured inside the access tube 12, thereby preventing the relative rotation of these components with respect to the access tube 12. Finally, the access tube 12 or handle 14 includes one or more guide pins 30 that are operable for visualizing the alignment of the access tube 12 with respect to the joint in an open or minimally-invasive surgical procedure, optionally under fluoroscopy/radiography. Specifically, these guide pins 30 can be aligned with the joint between the sacrum and the ilium, for example. In general, the access tube 12 acts as a guide relative to the joint in an open surgical procedure or a portal to the joint in a minimally-invasive surgical procedure.

Figure 2:
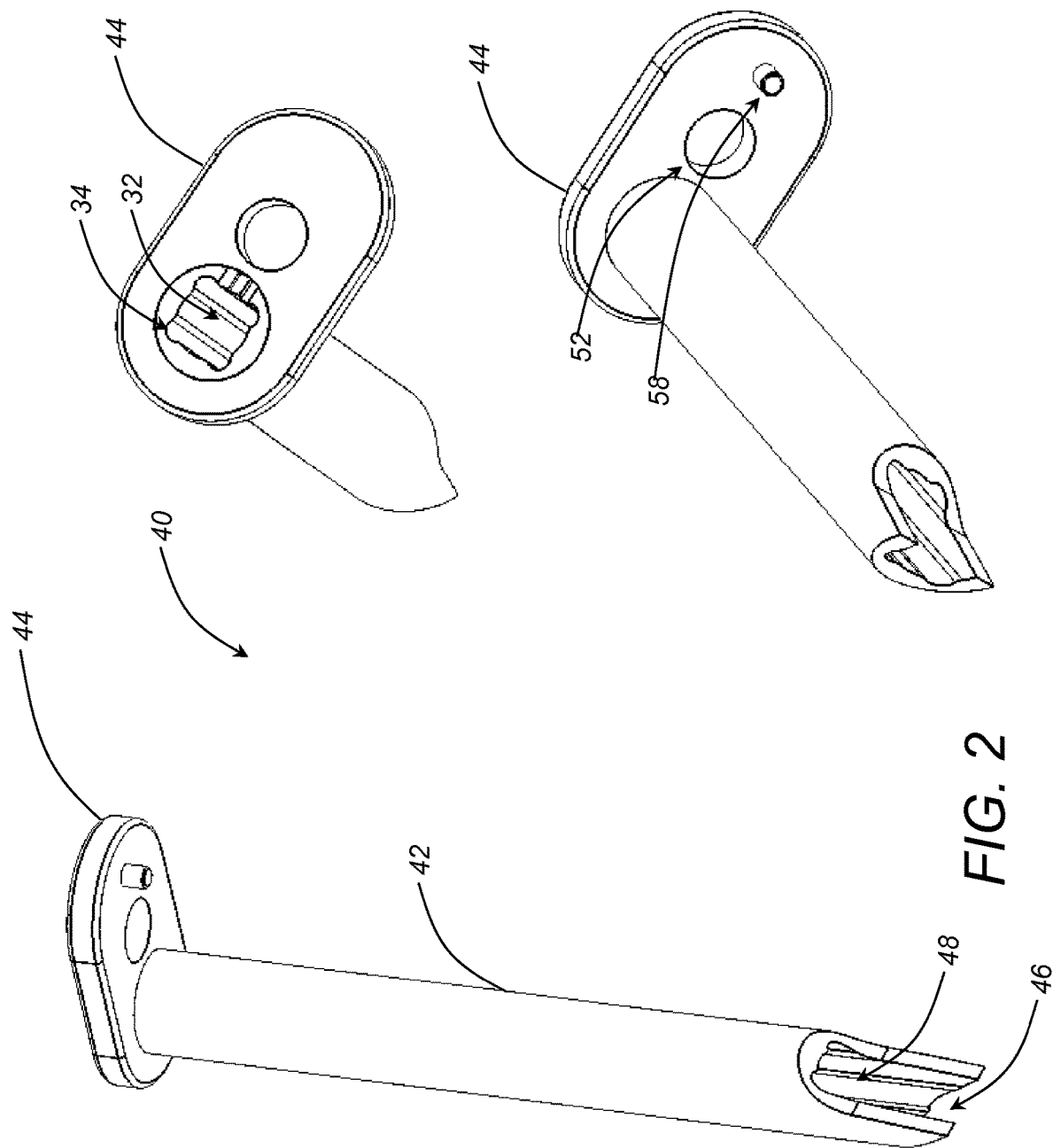
FIG. 2 is a series of perspective views of one exemplary embodiment of the drill guide tube of the present invention.

Referring now specifically to FIG. 2, in one exemplary embodiment, the drill guide tube 40 includes a cannulated drill tube 42 and a handle 44 coupled to the proximal end of the drill tube 42. In this exemplary embodiment, the drill tube 42 defines a central drill bore 32 with a plurality of smaller corner drill bores 34 disposed about the periphery of the central drill bore 32 in a generally square configuration. This and other exemplary configurations are described in greater detail below. However, all of the drill bores are configured to receive elongate drill bits (not illustrated) through the drill tube 42 such that a predetermined hole pattern can be drilled into and across the bony structures of the joint, providing a tailored void for receiving an implant, also described in greater detail below. The handle 44 is used to manipulate the drill tube 42, as well as to secure the drill tube 42 inside the access tube 12 (FIG. 1). The distal end of the drill tube 42 includes an angled end 46 defining one or more points, optionally including a cut away 48, that is configured and shaped to engage the sacroiliac joint, or another joint, such that the drill tube 42 is held in proper alignment, without penetrating too deeply. The angled end 46/cut away 48 of the drill tube 42 is preferably conformal with the angled end 16 (FIG. 1)/cut away 18 (FIG. 1) of the access tube 12 when the drill tube 42 is inserted into the access tube 12. Preferably, the drill tube 42 is made of a surgically compatible metal or plastic, and has a length of between about 120 and about 150 mm, an external diameter of between about 15 and about 20 mm, and an internal diameter of between about 3 and about 10 mm. The handle 44 is a generally paddle shaped component and may include a recess, finger contours, etc. The handle 44 includes a first port 52 that is configured to receive the shoulder stop of the guide pin 24 (FIG. 1). The handle 44 also includes pin 58 that is configured to engage the corresponding second port 28 (FIG. 1) of the handle 14 (FIG. 1) of the access tube 12 when the drill tube 42 is inserted into the access tube 12, thereby preventing the relative rotation of the drill tube 42 with respect to the access tube 12. In general, the drill tube 42 acts as a drill guide relative to the joint in an open surgical procedure or a minimally-invasive surgical procedure.

Figure 3:
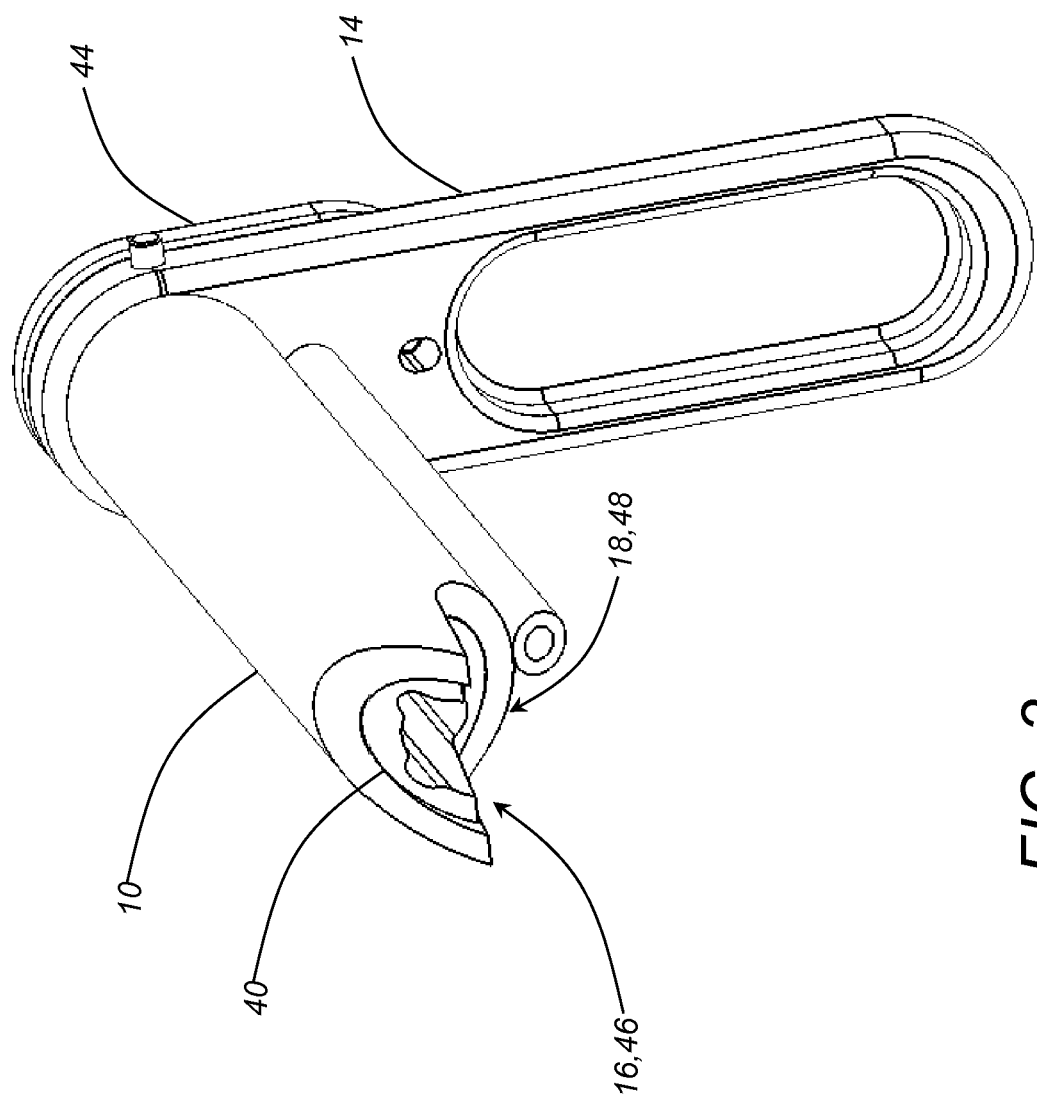
FIG. 3 is a perspective view of one exemplary embodiment of the portal tube and the drill guide tube of the present invention in an assembled configuration.

FIG. 3 illustrates the portal tube 10 and the drill guide tube 40 in an assembled configuration, highlighting that the angled end 46/cut away 48 of the drill guide tube 40 is conformal with the angled end 16/cut away 18 of the portal tube 10 when the drill guide tube 40 is inserted into the portal tube 10. The orientation of the handles 14 and 44 is also coincident.

Figure 4:
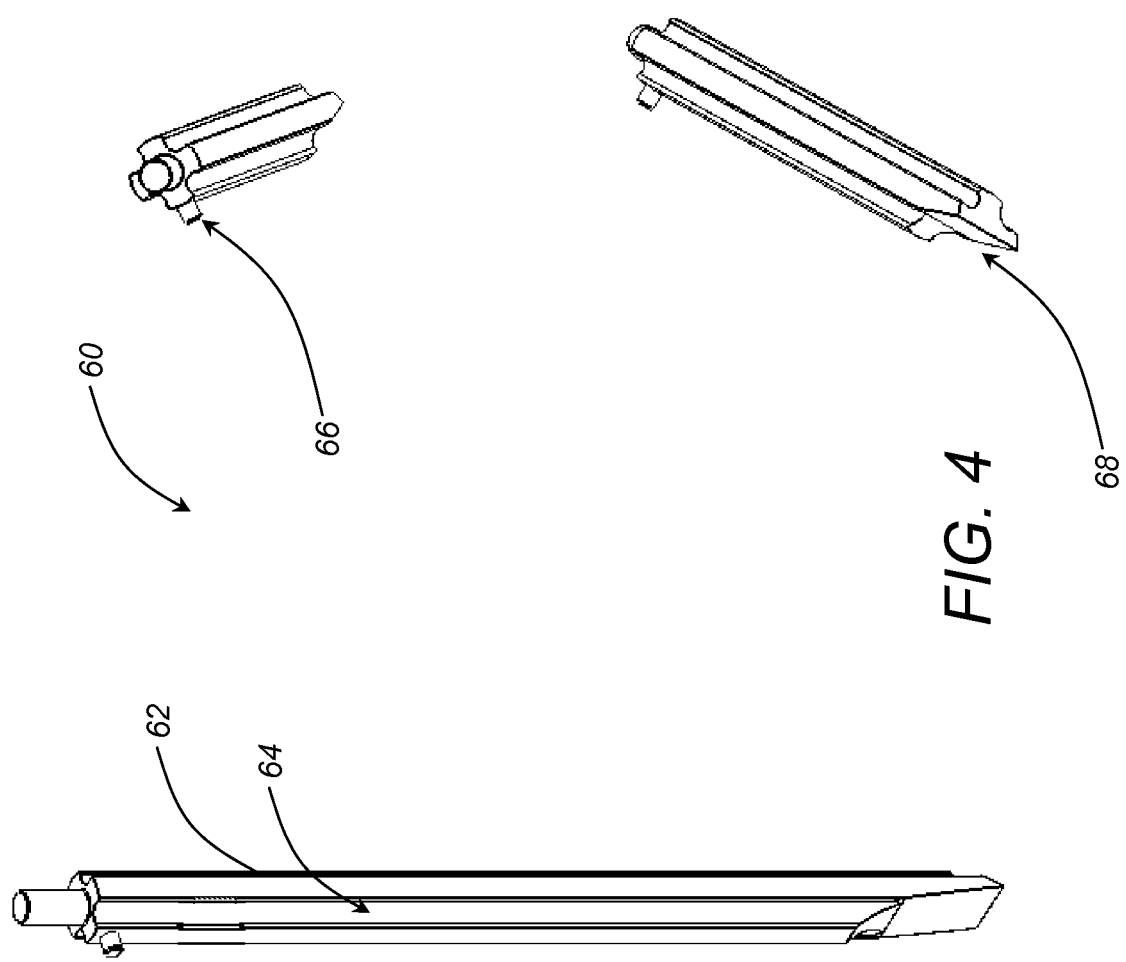
FIG. 4 is a series of perspective views of one exemplary embodiment of the drill guide of the present invention.

Referring now specifically to FIG. 4, in one exemplary embodiment, the drill guide 60 includes an elongate shaft 62 defining a plurality of drill bit receiving channels 64 disposed around the periphery and along the major axis thereof. The elongate shaft 62 is disposed within the drill guide tube 40 (FIGS. 2 and 3), which is disposed within the portal tube 10 (FIGS. 1 and 3). A key feature 66 protrudes from the proximal end of the elongate shaft 62 and is configured to engage a corresponding recess (not illustrated) manufactured into the handle 14 or 44 of either the portal tube 10 or the drill guide tube 40 or the proximal end of portal tube 10 or the drill guide tube 40, thereby preventing rotation of the drill elongate shaft 62 within the drill guide tube 40. In the exemplary embodiment illustrated, the elongate shaft 62 defines four drill bit receiving channels 64 disposed evenly around the periphery and along the major axis of the elongate shaft. Preferably, the drill guide 60 is made of a surgically compatible metal or plastic, and has a length of between about 120 and about 150 mm and an external diameter of between about 15 and about 20 mm. Each of the drill bit receiving channels 64 has a diameter of between about 2.5 and about 5 mm. Optionally, the distal end of the drill guide 60 includes an angled end 68 that is conformal with the angled end 16 (FIGS. 1 and 3)/cut away 18 (FIGS. 1 and 3) of the access tube 12 (FIG. 1) and the angled end 46 (FIGS. 2 and 3)/cut away 48 (FIGS. 2 and 3) of the drill tube 42 (FIG. 2) when the drill tube 42 is inserted into the access tube 12.

Figure 5:
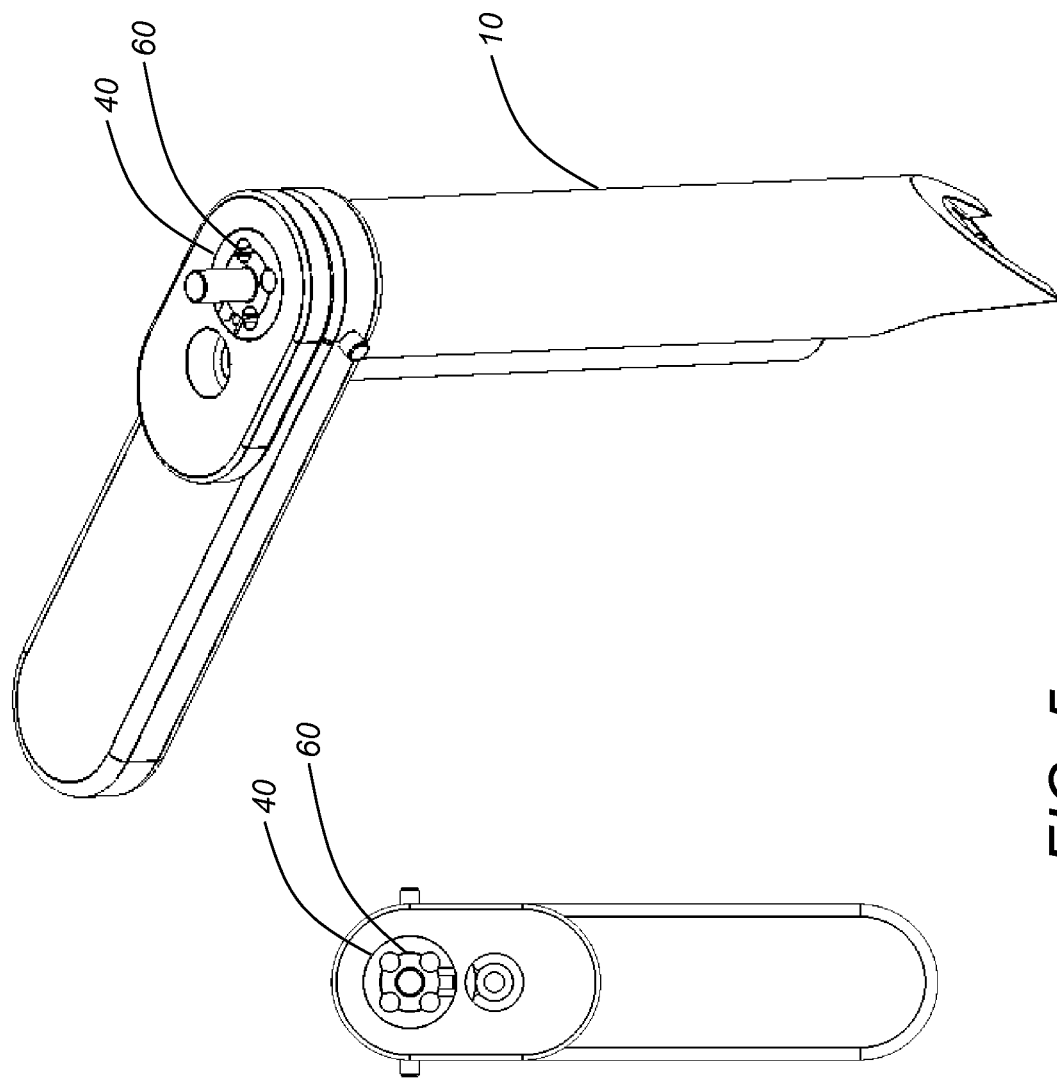
FIG. 5 is a perspective view and a top planar view of one exemplary embodiment of the portal tube, the drill guide tube, and the drill guide of the present invention in an assembled configuration.

FIG. 5 illustrates the portal tube 10, the drill guide tube 40, and the drill guide 60 in an assembled configuration.

Figure 6:
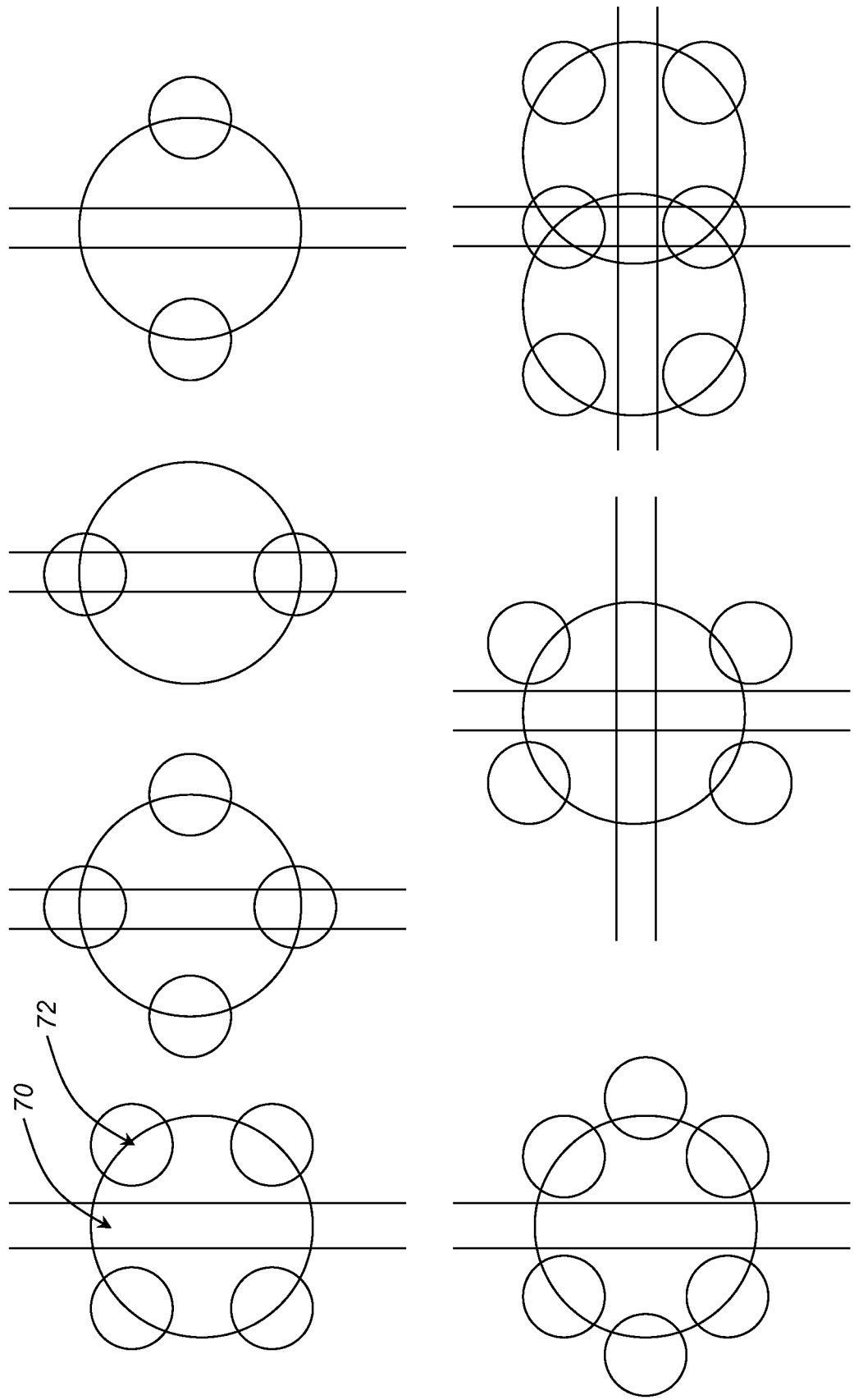
FIG. 6 is a series of schematic diagrams of exemplary drilling patterns that can be utilized in conjunction with/provided by the present invention.

FIG. 6 illustrates exemplary drilling patterns that can be utilized in conjunction with/provided by the present invention. The commonality among these drilling patterns is that they each include a major bore 70 that is drilled into/across the joint and one or more minor bores 72 that are drilled into/across the joint overlapping the major bore 70. In practice, the minor bores 72 can be drilled first with the drill guide 60 (FIGS. 4 and 5) inserted into the drill guide tube 40 (FIGS. 2, 3, and 5) inserted into the portal tube 10 (FIGS. 1, 3, and 5), with the major bore 70 drilled second with the drill guide 60 removed. Alternatively, the major bore 70 can be drilled first without the drill guide 60 inserted into the drill guide tube 40, with the minor bores 72 drilled second with the drill guide 60 inserted into the drill guide tube 40 inserted into the portal tube 10. Multiple major bores 70 can also be utilized, with the appropriate drill guide tube 40 and/or adjustment of the position of the portal tube 10 and/or drill guide tube 40 between the drilling of each major bore 70 and/or the minor bores 72. The resulting drilling pattern can thus for a rough square recess (illustrated), a rough diamond recess (illustrated), a rough H recess (illustrated), a rough rectangle recess (illustrated), etc. into which a corresponding implant can subsequently be impacted and press fit, as described below. It will be readily apparent to those of ordinary skill in the art that, using a variety of sizes and locations of drilled holes, a wide array of implant receiving holes can be created in terms of size and shape.

Figure 7:
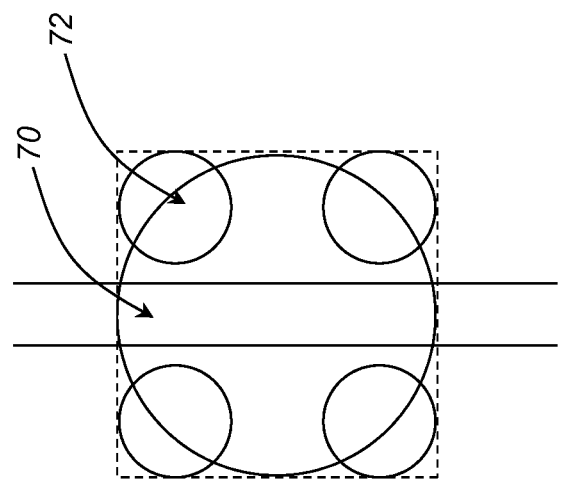
FIG. 7 is a series of schematic diagrams of another exemplary drilling pattern that can be utilized in conjunction with/provided by the present invention.
Figure 7:
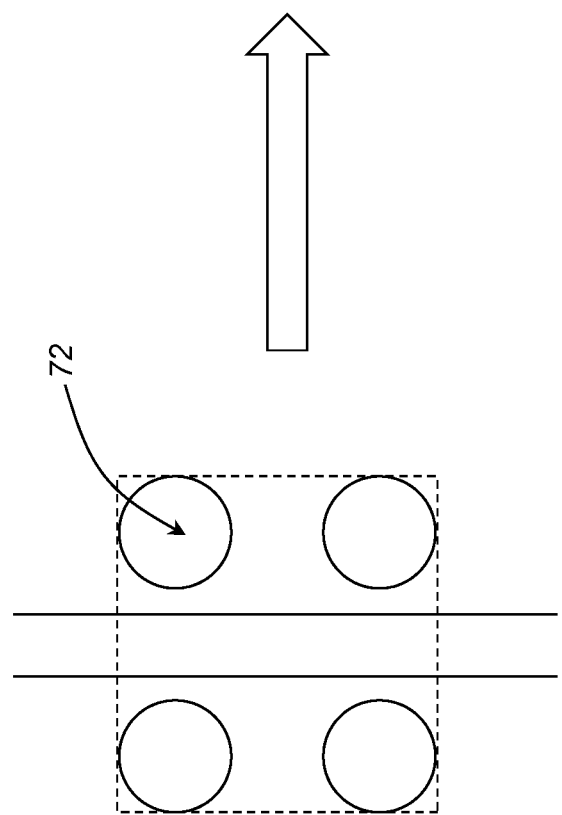

FIG. 7 is a series of schematic diagrams of another exemplary drilling pattern that can be utilized in conjunction with/provided by the present invention, highlighting that the major/minor bores 70 and 72 can be drilled in any order to form the predetermined void shape that is suitable for receiving the implant (not illustrated).

Figure 8:
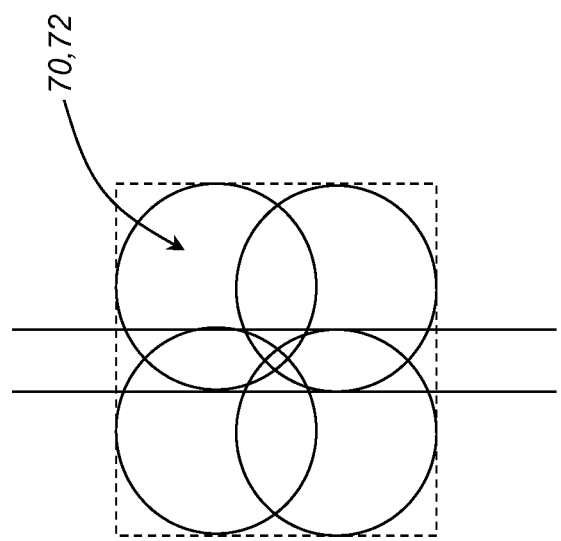
FIG. 8 is a schematic diagram of a further exemplary drilling pattern that can be utilized in conjunction with/provided by the present invention.

FIG. 8 is a schematic diagram of a further exemplary drilling pattern that can be utilized in conjunction with/provided by the present invention, highlighting that the major/minor bores 70 and 72 may all be similarly sized to form the predetermined void shape that is suitable for receiving the implant (not illustrated).

Figure 9:
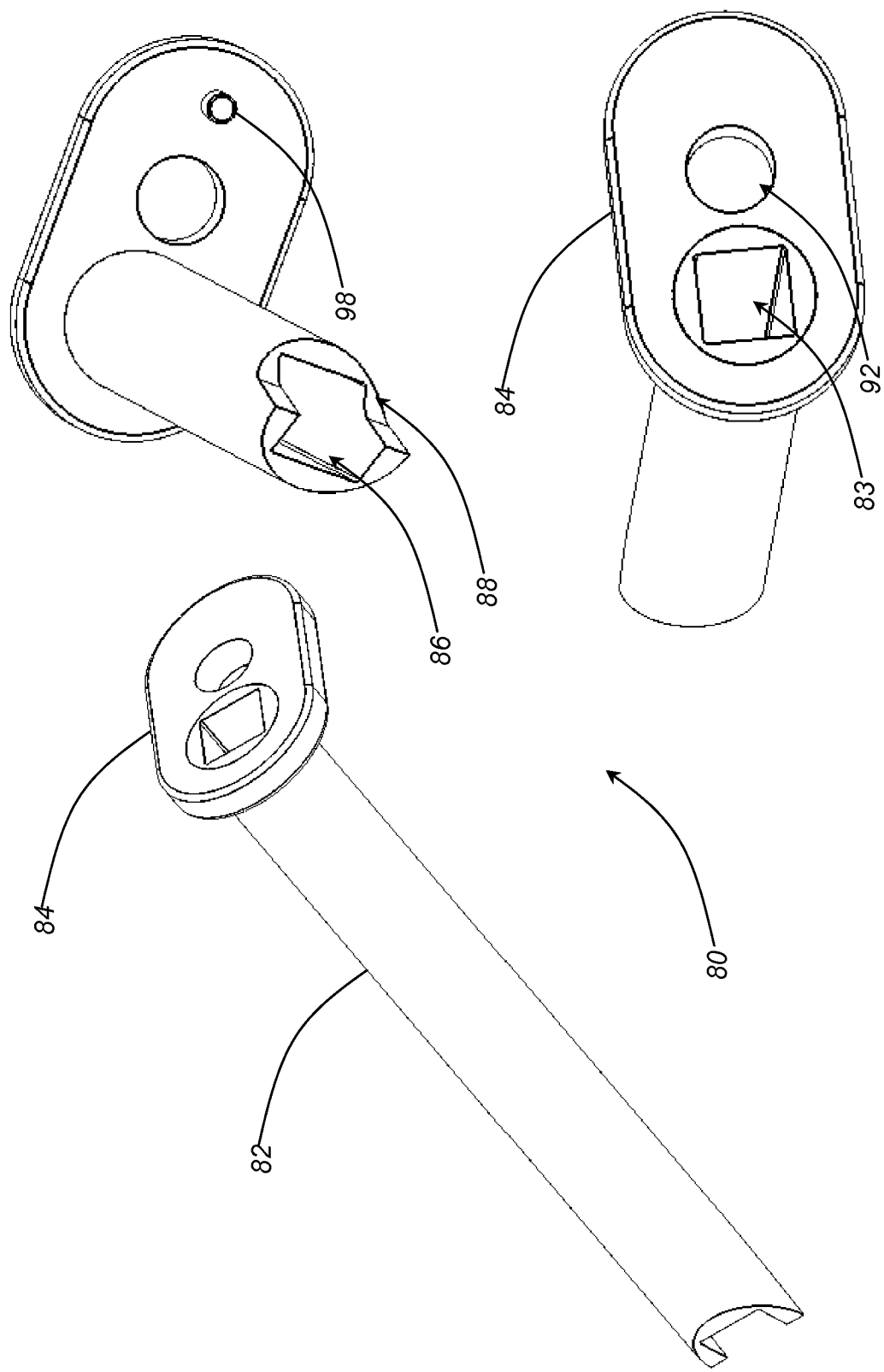
FIG. 9 is a series of perspective views of one exemplary embodiment of the implant guide tube of the present invention.

Referring now specifically to FIG. 9, in one exemplary embodiment, the implant guide tube 80 includes a cannulated implant tube 82 and a handle 84 coupled to the proximal end of the implant tube 82. In this exemplary embodiment, the implant tube 82 defines an implant bore 83 having a generally square shape through which a corresponding generally square implant is disposed in a generally square implant receiving hole formed as described above. It will be readily apparent to those of ordinary skill in the art that other shapes could be used equally. The handle 84 is used to manipulate the implant tube 82, as well as to secure the implant tube 82 inside the access tube 12 (FIG. 1) after the drill tube 42 (FIG. 2) is removed subsequent to drilling, for example. The distal end of the implant tube 82 includes an angled end 86, optionally including a cut away 88, that is configured and shaped to engage the sacroiliac joint, or another joint, such that the implant tube 82 is held in proper alignment, without penetrating too deeply. The angled end 86/cut away 88 of the implant tube 82 is preferably conformal with the angled end 16 (FIGS. 1 and 3)/cut away 18 (FIGS. 1 and 3) of the access tube 12 when the implant tube 82 is inserted into the access tube 12.

Preferably, the implant tube 82 is made of a surgically compatible metal or plastic, and has a length of between about 120 and about 150 mm, an external diameter of between about 15 and about 20 mm, and an internal width of between about 7 and about 12 mm. The handle 84 is a generally paddle shaped component and may include a recess, finger contours, etc. The handle 84 includes a first port 92 that is configured to receive the shoulder stop of the guide pin 24 (FIG. 1). The handle 84 also includes pin 98 that is configured to engage the corresponding second port 28 (FIG. 1) of the handle 14 (FIGS. 1 and 3) of the access tube 12 when the implant tube 82 is inserted into the access tube 12, thereby preventing the relative rotation of the implant tube 82 with respect to the access tube 12. In general, the implant tube 82 acts as an implant alignment and insertion guide relative to the joint in an open surgical procedure or a minimally-invasive surgical procedure.

Figure 10:
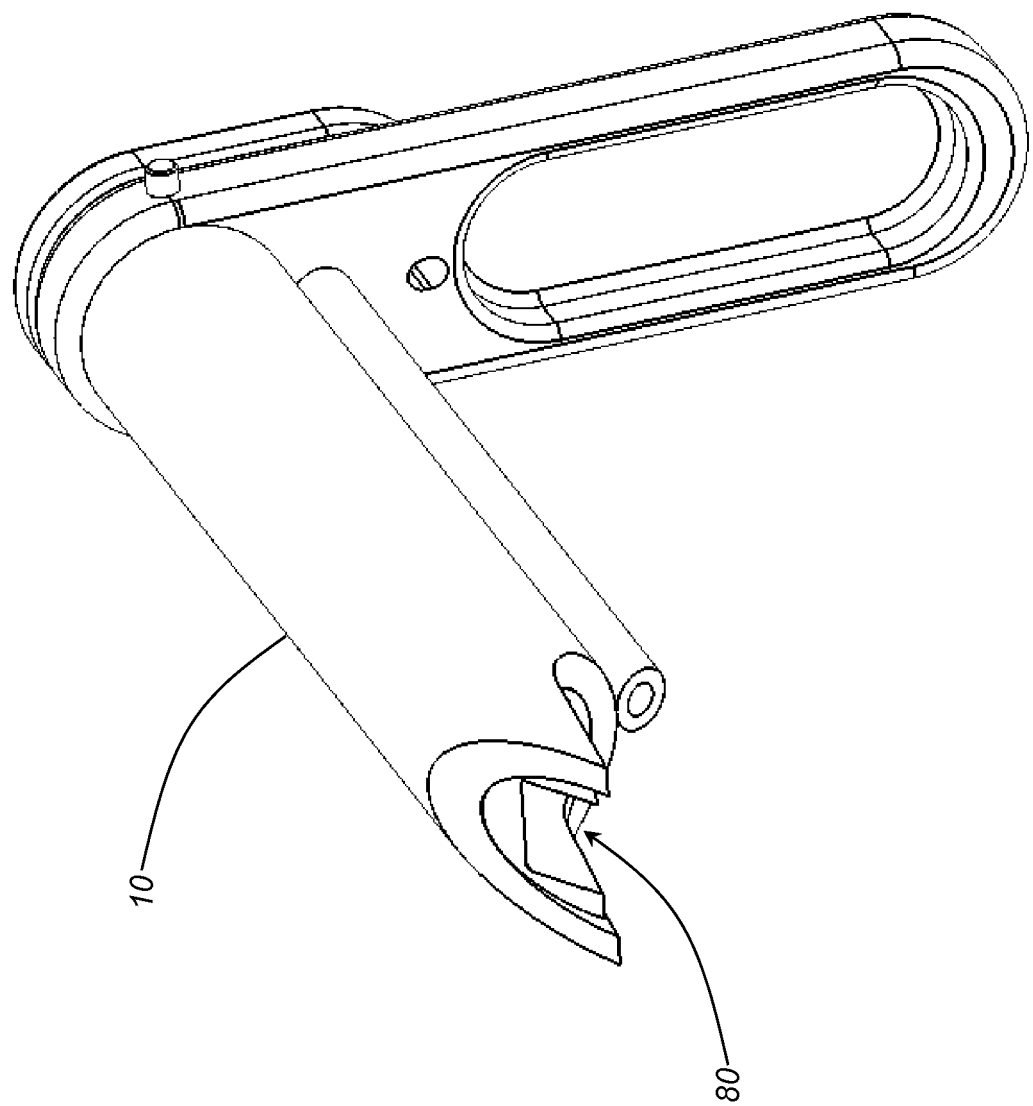
FIG. 10 is a perspective view of one exemplary embodiment of the portal tube and the implant guide tube of the present invention in an assembled configuration.

FIG. 10 illustrates the portal tube 10 and the implant guide tube 80 in an assembled configuration.

Figure 11:
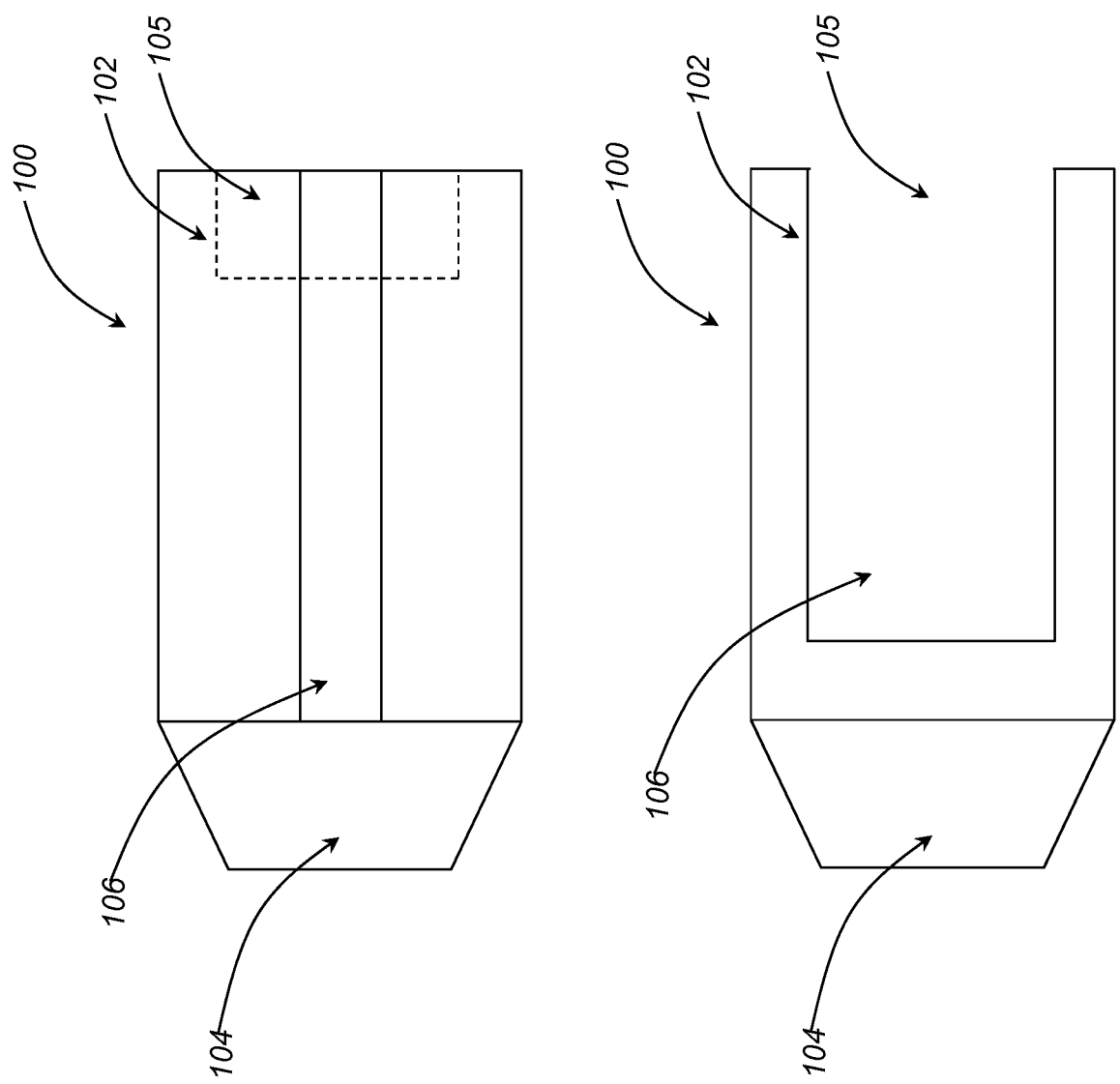
FIG. 11 is a planar view of one exemplary embodiment of the implant of the present invention.

Referring now specifically to FIG. 11, in one exemplary embodiment, the implant 100 of the present invention includes a body portion 102 and, optionally, a tapered tip portion 104. The tapered tip portion 104 aides in translating the implant into and through the implant guide tube 80 and press fitting the implant 100 into the hole prepared by the drilling techniques described above. Once placed, the body portion 102 promotes stabilization/fusion of the sacroiliac or other joint, and may also optionally provide or secure a desired degree of translation and/or distraction of the joint. Accordingly, it is desirable that the implant 100 have roughly the same shape perpendicular to its primary axis as the hole prepared by the drilling techniques described above. The implant may be made of a surgically compatible metal or plastic, bone allograft material, or the like. Typically, the implant 100 has a length of between about 17 and about 25 mm and a width or thickness of between about 7 and about 15 mm. Optionally, the body portion 102 defines one or more internal or external voids or channels 106 that is/are configured to receive bone graft material, thereby promoting bony fusion of the joint. Optionally, the body portion 102 also defines one or more internal or external voids or channels 105 that is/are configured to receive a placement/impaction tool, such as that described below. Finally, the body portion 102 may include one or more external fins, friction structures, or the like for preventing the implant 100 from backing out of the hole prepared by the drilling techniques described above. In practice, the implant 100 may be "over-impacted" into the hole prepared by the drilling techniques described above such that a bone "cap" of bone fusion promoting material or the like can be disposed on top of the implant 100. It should be noted that, in this regard, bone fusion promoting material can be placed in the hole before and/or after the implant 100 is impacted into the hole.

Referring now specifically to FIG. 12, in one exemplary embodiment, the implant impaction tool 110 of the present invention includes an elongate body portion 112 that substantially conforms to the internal shape of the implant guide tube 80 (FIGS. 9 and 10) and a handle portion 114. The implant impaction tool 110 is used to translate the implant 100 (FIG. 11) through the implant guide tube 80 and press fit the implant 100 into the hole prepared by the drilling techniques described above. Accordingly, the elongate body portion 112 has a length of between about 135 and about 150 mm and the handle portion or a separate shoulder stop may act as a penetration depth limiter.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. A joint fixation method, comprising:
   drilling a major bore in a joint, said major bore having a major longitudinal axis;
   drilling four or more minor bores in the joint, wherein the four or more minor bores are parallel to said major longitudinal axis and are radially disposed about a periphery of and partially overlap the major bore, said four or more minor bores positioned with respect to said major bore to leave at least one portion of a spandrel extending into a collective cross sectional shape of said major bore and said four or more minor bores; and disposing an implant in said major bore and said four or more minor bores, wherein a cross-sectional shape of said implant approximates said collective cross-sectional shape of said major bore and said four or more minor bores, said at least one portion of said spandrel impinging on a side surface of said implant to provide an interference fit between said major bore and said four or more minor bores and said implant, securing said implant in position.

2. The method of claim 1, further comprising, prior to drilling the major bore or the four or more minor bores, disposing a portal tube adjacent to the joint, thereby providing access to and stabilizing the joint.

3. The method of claim 2, further comprising securing the portal tube to the joint using a guide pin.

4. The method of claim 2, further comprising, prior to drilling said major bore or said four or more minor bores, disposing a drill guide tube concentrically within said portal tube.

5. The method of claim 4, further comprising drilling said major bore through said drill guide tube.

6. The method of claim 4, further comprising drilling said four or more minor bores through said drill guide tube.

7. The method of claim 4, further comprising, prior to drilling said four or more minor bores, disposing a drill guide concentrically within said drill guide tube.

8. The method of claim 1, further comprising, subsequent to drilling said major bore and said four or more minor bores, disposing an implant guide tube concentrically within a portal tube.

9. The method of claim 8, wherein said implant guide tube defines an internal channel that has a cross-sectional shape that substantially conforms to the cross-sectional shape of said implant, and wherein said implant is disposed in said major bore and said four or more minor bores through the internal channel of said implant guide tube.

10. The method of claim 9, wherein said implant is disposed in said major bore and said four or more minor bores through said implant guide tube using an elongate impaction tool that has a cross-sectional shape that substantially conforms to the cross-sectional shape of said internal channel of said implant guide tube.

11. The method of claim 1, wherein said implant comprises one or more recesses configured to hold a bone graft material.

12. The method of claim 1, wherein said joint comprises a sacroiliac joint.

* * * * *